United States Patent
Walther et al.

(10) Patent No.: US 8,383,772 B2
(45) Date of Patent: Feb. 26, 2013

(54) ANG-(1-7) RECEPTOR AGONIST

(75) Inventors: Thomas Walther, Angermünde (DE); Wolfgang Kuebler, Berlin (DE)

(73) Assignee: Charite Universitatsmedizin Berlin, Berlin (DE)

( * ) Notice: Subject to any disclaimer, the term of this patent is extended or adjusted under 35 U.S.C. 154(b) by 0 days.

(21) Appl. No.: 13/590,894

(22) Filed: Aug. 21, 2012

(65) Prior Publication Data

US 2012/0321701 A1 Dec. 20, 2012

Related U.S. Application Data

(63) Continuation of application No. 13/063,685, filed as application No. PCT/EP2009/006619 on Sep. 11, 2009.

(30) Foreign Application Priority Data

Sep. 12, 2008 (EP) .................................. 08016142

(51) Int. Cl.
| | |
|---|---|
| A61K 38/04 | (2006.01) |
| A61K 38/00 | (2006.01) |
| A61K 51/00 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl. ........ 530/329; 514/21.7; 514/1.1; 530/333; 424/1.69

(58) Field of Classification Search .................. None
See application file for complete search history.

(56) References Cited

U.S. PATENT DOCUMENTS

| | | | |
|---|---|---|---|
| 6,235,766 B1 | 5/2001 | Heitsch et al. | |
| 2003/0203834 A1* | 10/2003 | Tallant et al. ..................... | 514/1 |
| 2005/0119180 A1* | 6/2005 | Roks et al. ....................... | 514/12 |
| 2008/0159962 A1* | 7/2008 | Penninger et al. ............... | 424/45 |
| 2011/0281805 A1* | 11/2011 | Walther et al. ................ | 514/21.7 |

FOREIGN PATENT DOCUMENTS

| | | |
|---|---|---|
| WO | 2006/128266 A2 | 12/2006 |
| WO | 2007/000036 A2 | 1/2007 |
| WO | 2007/121546 A1 | 11/2007 |

OTHER PUBLICATIONS

Metzler et al. (Nature Structural Biol. 1997; 4:527-531) (available online).*
Lazar, et al. (Mol. Cell. Biol. 8:1247-1252, 1988 (available online).*
Chinese Office Action for corresponding Chinese Patent Application No. 200980135629.4, issued Jan. 30, 2012.
Jiang et al., "Angiotensin-converting enzyme inhibitor captopril attenuates ventilator-induced lung injury in rats", J. Appl. Physiol. 102:2098-2103 (2007).
Lula et al., "Study of angiotensin-(1-7) vasoactive peptide and its β-cyclodextrin inclusion complexes: complete sequence-specific NMR assignments and structural studies", Peptides, 28:2199-2210 (2007).
Santos et al., "Pharmacological effects of AVE 0991, a nonpeptide angiotensin-(1-7) receptor agonist", Cardiovascular Drug Reviews, 24(3-4):239-246 (2006).
International Search Report for PCT/EP2009/006619, dated Apr. 7, 2010.
Rubenfeld et al., "Incidence and outcomes of acute lung injury", N. Engl. J. Med., 353:1685-1693 (2005).
Zambon et al., "Mortality rates for patients with acute lung injury/ARDS have decreased over time", Chest, 133 (5):1120-1127 (2008).
Bachofen et al., "Structural alterations of lung parenchyma in the adult respiratory distress syndrome", Clin. Chest Med., 3:35-56 (1982).
Ware et al., "The acute respiratory distress syndrome", N. Engl. J. Med., 342:1334-1349 (2000).
Steinberg et al., "Efficacy and safety of corticosteroids for persistent acute respiratory distress syndrome", N. Engl. J. Med., 354:1671-1684 (2006).
The Acute Respiratory Distress Syndrome Network, "Randomized, placebo-controlled trial of lisofylline for early treatment of acute lung injury and acute respiratory distress syndrome", Crit. Care Med., 30:1-6 (2002).
The Acute Respiratory Distress Syndrome Network, "Ketoconazole for early treatment of acute lung injury and acute respiratory distress syndrome: a randomized controlled trial", JAMA, 283:1995-2002 (2000).
The Acute Respiratory Distress Syndrome Network, "Ventilation with lower tidal volumes as compared with traditional tidal volumes for acute lung injury and the acute respiratory distress syndrome", N. Engl. J. Med., 342:1301-1308 (2000).
Imai et al., "Angiotensin-converting enzyme 2 protects from severe acute lung failure", Nature, 436:112-116 (2005).
Wösten-van Asperen et al., "ACE mediates ventilator-induced lung injury in rats via angiotensin II but not bradykinin", Eur. Respir. J., 31:363-371 (2008).
Yao et al., "Losartan attenuates ventilator-induced lung injury", J. Surg. Res., 145:25-32 (2008).
He et al., "Angiotensin-converting enzyme inhibitor captopril prevents oleic acid-induced severe acute lung injury in rats", Shock, 28:106-111 (2007).
Jiang et al., "Angiotensin-converting enzyme inhibitor captopril attenuates ventilator-induced lung injury in rats", J. Appl. Physiol., 102:2098-2103 (2007).
Santos et al., "Angiotensin-(1-7) is an endogenous ligand for the G protein-coupled receptor Mas", Proc. Natl. Acad. Sci. USA, 100:8258-8263 (2003).

(Continued)

*Primary Examiner* — Maury Audet
(74) *Attorney, Agent, or Firm* — Fangli Chen; Brian E. Reese; Choate Hall & Stewart, LLP

(57) ABSTRACT

The application provides Ang-(1-7) receptor agonist peptides and their use for treating acute lung injury.

7 Claims, 4 Drawing Sheets

OTHER PUBLICATIONS

Kostenis et al., "G-protein-coupled receptor Mas is a physiological antagonist of the angiotensin II type I receptor", Circulation, 111:1806-1813 (2005).

Matthay, M.A., "Acute lung injury: conference summary", Chest, 116:119S-126S (1999).

Tabuchi et al., "Intravital microscopy of the murine pulmonary microcirculation", 104:338-346 (2008).

Hentschel et al., "Inhalation of the phosphodiesterase-3 inhibitor milrinone attenuates pulmonary hypertension in a rat model of congestive heart failure", Anesthesiology, 106:124-131 (2007).

Kuebler et al., "Measurement of neutrophil content in brain and lung tissue by a modified myeloperoxidase assay", Int. J. Microcirc. Clin. Exp., 16:89-97 (1996).

* cited by examiner

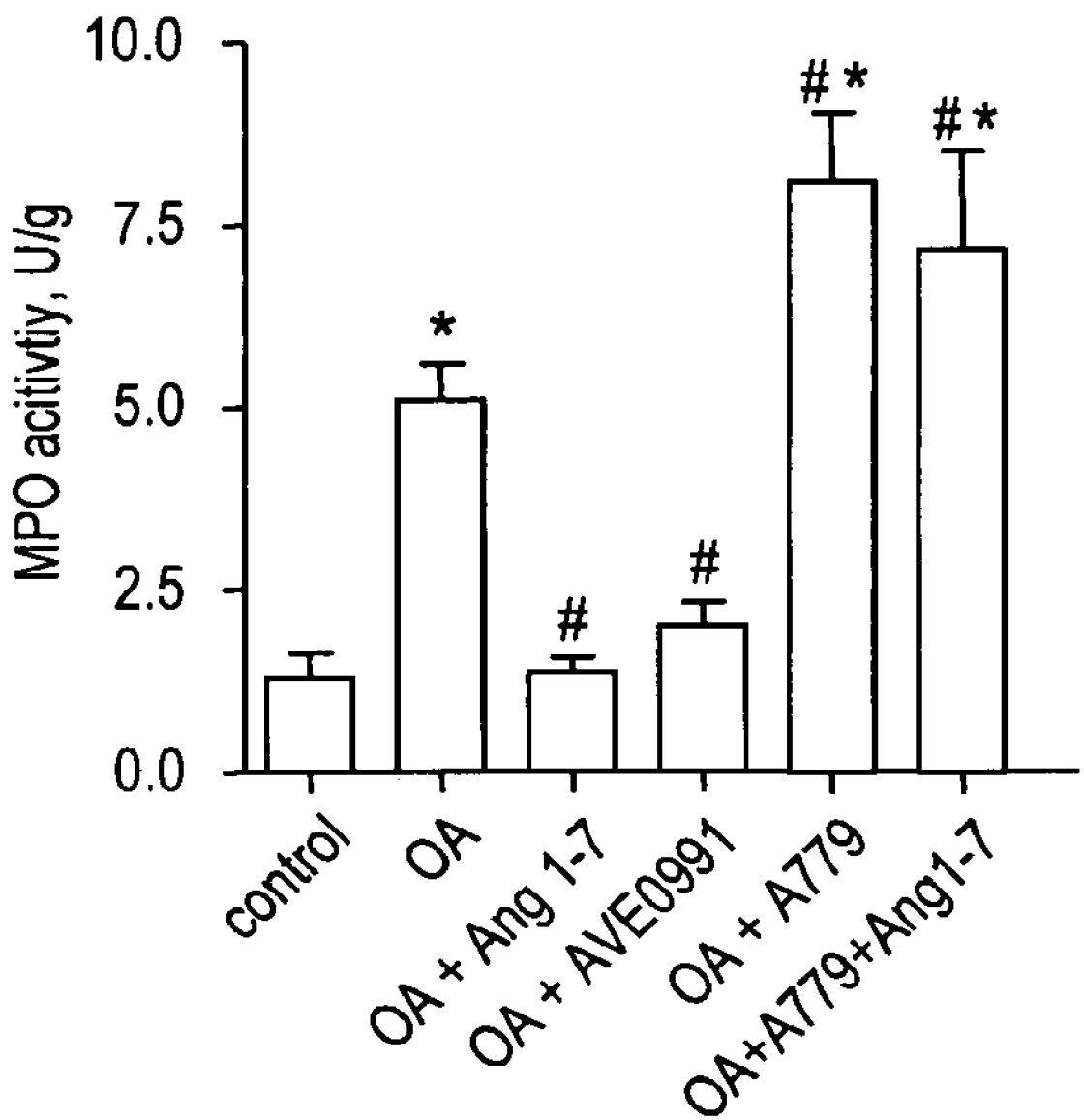

(a)

(b)

(a)

(b)

SEQUENCE LISTING

```
<160> NUMBER OF SEQ ID NOS: 9

<210> SEQ ID NO 1
<211> LENGTH: 7
<212> TYPE: PRT
<213> ORGANISM: Artificial
<220> FEATURE:
<223> OTHER INFORMATION: Ang-(1-7)

<400> SEQUENCE: 1

Asp Arg Val Tyr Ile His Pro
1               5

<210> SEQ ID NO 2
<211> LENGTH: 7
<212> TYPE: PRT
<213> ORGANISM: Artificial
<220> FEATURE:
<223> OTHER INFORMATION: Ang-(1-7) derivative

<400> SEQUENCE: 2

Asn Arg Val Ser Ile His Pro
1               5

<210> SEQ ID NO 3
<211> LENGTH: 7
<212> TYPE: PRT
<213> ORGANISM: Artificial
<220> FEATURE:
<223> OTHER INFORMATION: Ang-(1-7) derivative

<400> SEQUENCE: 3

Asn Arg Val Tyr Ile His Cys
1               5
```

```
<210> SEQ ID NO 4
<211> LENGTH: 7
<212> TYPE: PRT
<213> ORGANISM: Artificial
<220> FEATURE:
<223> OTHER INFORMATION: Ang-(1-7) derivative

<400> SEQUENCE: 4

Asn Arg Val Ser Ile His Cys
1               5

<210> SEQ ID NO 5
<211> LENGTH: 7
<212> TYPE: PRT
<213> ORGANISM: Artificial
<220> FEATURE:
<223> OTHER INFORMATION: NorLeu3-Ang-(1-7) peptide
<220> FEATURE:
<221> NAME/KEY: MOD_RES
<222> LOCATION: (3)..(3)
<223> OTHER INFORMATION: /replace="Nle"

<400> SEQUENCE: 5

Asn Arg Leu Tyr Ile His Pro
1               5

<210> SEQ ID NO 6
<211> LENGTH: 6
<212> TYPE: PRT
<213> ORGANISM: Artificial
<220> FEATURE:
<223> OTHER INFORMATION: Ang IV

<400> SEQUENCE: 6

Val Tyr Ile His Pro Phe
1               5

<210> SEQ ID NO 7
<211> LENGTH: 7
<212> TYPE: PRT
<213> ORGANISM: Artificial
<220> FEATURE:
<223> OTHER INFORMATION: Ang III

<400> SEQUENCE: 7

Arg Val Tyr Ile His Pro Phe
1               5

<210> SEQ ID NO 8
<211> LENGTH: 7
<212> TYPE: PRT
<213> ORGANISM: Artificial
<220> FEATURE:
<223> OTHER INFORMATION: A779
<220> FEATURE:
<221> NAME/KEY: MOD_RES
<222> LOCATION: (7)..(7)
<223> OTHER INFORMATION: /replace="D-Ala"

<400> SEQUENCE: 8

Asn Arg Val Tyr Ile His Ala
1               5

<210> SEQ ID NO 9
<211> LENGTH: 7
<212> TYPE: PRT
<213> ORGANISM: Artificial
<220> FEATURE:
<223> OTHER INFORMATION: D-Pro-Ang-(1-7)
```

```
<220> FEATURE:
<221> NAME/KEY: MOD_RES
<222> LOCATION: (7)..(7)
<223> OTHER INFORMATION: /replace="D-Pro"

<400> SEQUENCE: 9

Asn Arg Val Tyr Ile His Pro
1               5
```

ANG-(1-7) RECEPTOR AGONIST

CROSS-REFERENCE TO RELATED APPLICATIONS

This application is a continuation of U.S. application Ser. No. 13/063,685, filed Mar. 11, 2011, which is a national phase entry of International Application No. PCT/EP2009/006619, filed Sep. 11, 2009, published on Mar. 18, 2010 under International Publication No. WO2010/028845, which claims priority to EP Application No. 08016142.5, filed Sep. 12, 2008, the disclosures all of which are incorporated by reference in their entireties.

FIELD OF THE INVENTION

The present invention refers to a peptidic or non-peptidic angiotensin-(1-7) (Ang-(1-7)) receptor agonist, preferably a Mas receptor agonist, for the prevention and/or treatment of acute lung injury, preferably acute respiratory distress syndrome.

Sequence Listing

The present specification makes reference to a Sequence Listing (submitted electronically as a .txt file named "SequenceListing_ST25.txt" on Aug. 21, 2012. The .txt file was generated on Aug. 21, 2012 and is 2 kb in size. The entire contents of the Sequence Listing are herein incorporated by reference.

BACKGROUND OF THE INVENTION

With age-adjusted incidences of 86.2 per 100,000 person-years and overall mortality rates of ~43%, acute lung injury (ALI) and its most severe form, the acute respiratory distress syndrome (ARDS), remain a major cause of death in intensive care (1,2). The pathological hallmarks of the disease comprise diffuse alveolo-capillary injury and an increased lung permeability associated with a strong inflammatory response (3,4). These changes underlie the clinical presentation which is characterized by an acute onset, severe hypoxemia and a proteinaceous lung oedema. Despite a multitude of large multi-centric clinical trials to explore the potential of various therapeutic strategies including the use of glucocorticoids, ketoconazole, lisofylline, alprostadil, inhaled NO or supplemented surfactant (5-7), no therapeutic pharmacological intervention could so far improve the clinical outcome of ALI/ARDS. So far, the only evident improvement for the survival of ARDS patients has been achieved by the implementation of minimal invasive ventilation strategies with low tidal volumes as compared to the previously used high tidal volumes (8).

In a recent experimental study, Imai and co-workers could demonstrate that angiotensin converting enzyme 2 (ACE2), which converts Ang II to Ang-(1-7) by cleavage of one amino acid, protects mice from severe acute lung injury induced by acid aspiration or sepsis (9). The authors attributed this finding to the fact that ACE2 will decrease Ang II concentration and thus, reduce the activation of the Ang II type I receptor (AT1). This notion has triggered a series of studies demonstrating the effectiveness of AT1 receptor blockers or ACE inhibitors for the treatment of various forms of experimental acute lung injury (10-13).

Importantly however, the cleavage product of Ang II by ACE2, Ang-(1-7), is not an inert waste product of the angiotensin-pathway, but may exert active biological functions. Ang-(1-7) binds to the G protein-coupled receptor Mas (14) which appears to be a physiological antagonist of the AT1a receptor (15), and potentially to other receptors. Binding of Ang-(1-7) to its receptor(s) may thus contribute critically to the previously demonstrated beneficial effects of interventions in the angiotensin pathway on the pathology of ALI/ARDS.

The U.S. Pat. No. 6,235,766 refers to non-peptidic agonists of Ang-(1-7) receptors, and particularly discloses 1-(p-thienylbenzyl)imidazoles having a marked action on Ang-(1-7) receptors and mimicking the biological action of the effector hormone Ang-(1-7).

The international patent application WO 2006/128266 refers to the interaction between the Mas receptor and Ang-(1-7) or its analogues in the context of controlling the functions of the reproductive system.

The international patent application WO 2007/000036 refers to the use of peptidic or non-peptidic Mas receptor agonists and antagonists as apoptotic activity modulators.

The international patent application WO 2007/121546 refers to the use of peptidic or non-peptidic Mas receptor agonists for modulating metabolic activities related to the clinical manifestation of the metabolic syndrome or its complications.

We speculated that Ang-(1-7) or related agonists may represent a new and promising strategy for the treatment of ALI/ARDS. Thus, the object of the present invention is to provide means and methods for a pharmacological intervention in the patho-physiologic events underlying ALI/ARDS.

SUMMARY OF THE INVENTION

The object of the present invention is solved by an Ang-(1-7) receptor agonist for use in the prevention and/or treatment of an acute lung injury in a subject.

The object of the present invention is solved by a method for the prevention and/or treatment of an acute lung injury in a subject using an Ang-(1-7) receptor agonist.

The object of the present invention is further solved by a use of an Ang-(1-7) receptor agonist for the preparation of a pharmaceutical composition for the prevention and/or treatment of an acute lung injury in a subject.

The object of the present invention is further solved by a method of prevention and/or treatment of an acute lung injury by administering an Ang-(1-7) receptor agonist to a subject.

In one embodiment, the Ang-(1-7) receptor agonist is a Mas receptor agonist.

In one embodiment, the Ang-(1-7) receptor agonist interacts with a Mas receptor or a receptor associated with a Mas receptor.

In one embodiment, the Ang-(1-7) receptor agonist stimulates a receptor that physically interacts with a Mas receptor.

In one embodiment, the Ang-(1-7) receptor agonist stimulates a receptor that shares pharmacological similarities with a Mas receptor.

In one embodiment, the Ang-(1-7) receptor agonist is an Ang II metabolite sharing structural similarities with the Ang-(1-7) peptide.

In one embodiment, the receptor agonist is a peptidic or non-peptidic agonist.

In one embodiment, the peptidic agonist is an exogenous or endogenous Ang-(1-7) peptide comprising an amino acid sequence $Asp^1$-$Arg^2$-$Val^3$-$Tyr^4$-$Ile^5$-$His^6$-$Pro^7$ according to SEQ ID NO: 1 or is a derivative or analogue thereof.

In one embodiment, the peptidic agonist is a derivative or analogue of the Ang-(1-7) peptide, the derivative or analogue comprising an amino acid exchange, deletion or insertion. Preferably, the derivative or analogue has conserved or better agonistic properties.

In one embodiment, the peptidic agonist is a derivative or analogue of the Ang-(1-7) peptide, the derivative or analogue comprising an amino acid sequence $Asp^1$-$Arg^2$-$Val^3$-$Ser^4$-$Ile^5$-$His^6$-$Pro^7$ according to SEQ ID NO: 2, $Asp^1$-$Arg^2$-$Val^3$-$Tyr^4$-$Ile^5$-$His^6$-$Cys^7$ according to SEQ ID NO: 3 or $Asp^1$-$Arg^2$-$Val^3$-$Ser^4$-$Ile^5$-$His^6$-$Cys^7$ according to SEQ ID NO: 4.

In one embodiment, the peptidic agonist is a peptide comprising an amino acid sequence according to SEQ ID NO: 2, SEQ ID NO: 3 or SEQ ID NO: 4.

In one embodiment, the peptidic agonist is an exogenous or endogenous NorLeu3-Ang-(1-7) peptide comprising an amino acid sequence $Asp^1$-$Arg^2$-$NorLeu^3$-$Tyr^4$-$Ile^5$-$His^6$-$Pro^7$ according to SEQ ID NO: 5 or is a derivative or analogue thereof.

In one embodiment, the peptidic agonist is an exogenous or endogenous Ang IV peptide comprising an amino acid sequence $Val^1$-$Tyr^2$-$Ile^3$-$His^4$-$Pro^5$-$Phe^6$ according to SEQ ID NO: 6 or is a derivative or analogue thereof.

In one embodiment, the peptidic agonist is an exogenous or endogenous Ang III peptide comprising an amino acid sequence $Arg^1$-$Val^2$-$Tyr^3$-$Ile^4$-$His^5$-$Pro^6$-$Phe^7$ according to SEQ ID NO: 7 or is a derivative or analogue thereof.

In one embodiment, the non-peptidic agonist is selected from the group of 1-(p-thienylbenzyl)imidazole compounds, and preferably is Ave 0991 (i.e. 5-formyl-4-methoxy-2-phenyl-1[[4-[2-(ethylaminocarbonylsulfonamido)-5-isobutyl-3-thienyl]phenyl]methyl]-imidazole).

In one embodiment, the acute lung injury is an acute respiratory distress syndrome.

In one embodiment, the acute lung injury is related to a pulmonary (direct) or an extrapulmonary (indirect) lung injury.

In one embodiment, the pulmonary lung injury is selected from the group consisting of inhalation trauma, aspiration trauma, toxic lung oedema, lung infection, preferably pneumonia, lung contusion, and embolism.

In one embodiment, the extrapulmonary lung damage is associated with a disorder selected from the group consisting of sepsis, systemic inflammatory response syndrome (SIRS), polytrauma, shock, burn, acute pancreatitis, drug intoxication, alcohol abuse, chronic lung disease, mass transfusion, disseminated intravascular coagulation, erythema, and autoimmune lung disease.

In one embodiment, the subject is a mammal, preferably a human, most preferably an adult human.

The object of the present invention is further solved by a pharmaceutical composition comprising an Ang-(1-7) receptor agonist for use in the prevention and/or treatment of an acute lung injury in a subject.

The object of the present invention is further solved by a method for the prevention and/or treatment of an acute lung injury in a subject using a pharmaceutical composition comprising an Ang-(1-7) receptor agonist.

In one embodiment of the pharmaceutical composition, the Ang-(1-7) receptor agonist is a Mas receptor agonist.

In one embodiment of the pharmaceutical composition, the receptor agonist is a peptidic or non-peptidic agonist.

In one embodiment of the pharmaceutical composition, the peptidic agonist is an Ang-(1-7) peptide comprising an amino acid sequence according to SEQ ID NO: 1 or is a derivative or analogue thereof.

In one embodiment of the pharmaceutical composition, the peptidic agonist is a peptide comprising an amino acid sequence according to SEQ ID NO: 2, SEQ ID NO: 3 or SEQ ID NO: 4.

In one embodiment of the pharmaceutical composition, the peptidic agonist is a peptide comprising an amino acid sequence according to SEQ ID NO: 5 or is a derivative or analogue thereof.

In one embodiment of the pharmaceutical composition, the peptidic agonist is an Ang IV peptide comprising an amino acid sequence according to SEQ ID NO: 6 or is a derivative or analogue thereof.

In one embodiment of the pharmaceutical composition, the peptidic agonist is an Ang III peptide comprising an amino acid sequence according to SEQ ID NO: 7 or is a derivative or analogue thereof.

In one embodiment of the pharmaceutical composition, the non-peptidic agonist is selected from the group of 1-(p-thienylbenzyl)imidazole compounds, and preferably is Ave 0991 (i.e. 5-formyl-4-methoxy-2-phenyl-1-[[4-[2-(ethylaminocarbonylsulfonamido)-5-isobutyl-3-thienyl]phenyl]methyl] imidazole).

In one embodiment of the pharmaceutical composition, the acute lung injury is an acute respiratory distress syndrome.

In one embodiment of the pharmaceutical composition, the acute lung injury is related to a pulmonary (direct) or an extrapulmonary (indirect) lung injury.

In one embodiment of the pharmaceutical composition, the pulmonary lung injury is selected from the group consisting of inhalation trauma, aspiration trauma, toxic lung oedema, lung infection, preferably pneumonia, lung contusion, and embolism.

In one embodiment of the pharmaceutical composition, the extrapulmonary lung damage is associated with a disorder selected from the group consisting of sepsis, polytrauma, shock, burn, acute pancreatitis, drug intoxication, alcohol abuse, chronic lung disease, mass transfusion, disseminated intravascular coagulation, erythema, and autoimmune lung disease.

In one embodiment of the pharmaceutical composition, the subject is a mammal, preferably a human, most preferably an adult human.

In one embodiment, the pharmaceutical composition is formulated for a parenteral or enteral administration, preferably for a parenteral administration by the route of inhalation, infusion or injection. A pharmaceutical composition formulated for an oral, an intramuscular, an intravenous, a subcutaneous, a topical, a transdermal, a rectal, a vaginal, a pulmonary, an intranasal, an intrabuccal, or a sublingual administration is also considered.

In one embodiment, the pharmaceutical composition is formulated as a tablet, a pill, a capsule, granules, a syrup, a spray, an aerosol, a liposomal composition, an ointment, a suppository, an implant, a plaster, or a slow release formulation.

In one embodiment, the pharmaceutical composition further comprises one or more pharmacologically inert and pharmaceutically acceptable excipients such as a polymer carrier, a disintegration agent, a lubricant, a solvent, or a swelling agent.

The term "receptor agonist" refers to an agent being capable of activating a receptor, i.e. eliciting a receptor response. The term "Ang-(1-7) receptor agonist" refers to an agent being capable of activating a receptor that is also activated by Ang-(1-7). The term "Mas receptor agonist" refers to an agent being capable of activating the G protein-coupled Mas receptor. As an adequate receptor response, a direct or indirect (due to a receptor physically interacting with Mas) G protein-mediated signalling cascade downstream from the receptor is initiated resulting in e.g. arachidonic acid release, $PGI_2$ formation, NO formation, and/or cGMP generation.

Since Ang-(1-7) signalling is blocked by A779 ([D-Ala$^7$-Ang-(1-7); Asp$^1$-Arg$^2$-Val$^3$-Tyr$^4$-Ile$^5$-His$^6$-D-Ala$^7$, SEQ ID NO: 8) and/or D-Pro$^7$-Ang-(1-7) (Asp$^1$-Arg$^2$-Val$^3$-Tyr$^4$-Ile$^5$-His$^6$-D-Pro$^7$, SEQ ID NO: 9), a further characteristic of an Ang-(1-7) agonist is the inhibition of its effects by A779 and/or D-Pro$^7$-Ang-(1-7). Further non-competitive or competitive inhibitors are also considered.

The term "peptidic agonist" refers to a compound comprising one or more peptide bonds. The term encompasses compounds consisting of a pure peptidic structure, i.e. a peptide composed of two or more amino acids, as well as compounds comprising peptidic and non-peptidic structures.

The term "non-peptidic agonist" refers to a compound not comprising a peptide bond. Preferably, such a compound is of low molecular weight, i.e. a small molecule.

The term "derivative" means a compound differing from another compound by a structural modification, for example by replacement of one atom or a group of atoms or a functional group with another atom or group of atoms or functional group.

The term "analogue" means a compound which is similar in structure or function to another compound.

The term "exogenous Ang-(1-7)" means Ang-(1-7) that is produced outside of the subject's body to be treated and is exogenously applied. This, however, does not exclude that Ang-(1-7) is produced in e.g. a transgenic animal not to be treated. Generally considered is Ang-(1-7) produced by biosynthesis or conventional lab synthesis, e.g. solid-phase synthesis.

The term "endogenous Ang-(1-7)" means that Ang-(1-7) is endogenously produced by the subject's body to be treated. An (increased) endogenous production of Ang-(1-7) can be the result of a stimulation of its generation from Ang II, e.g. by pharmacologically activating ACE2, by blocking the AT1a receptor, or by inhibiting the degradation of Ang II to Ang III by APA. Similarly, endogenous Ang-(1-7) production can be increased by stimulation of its generation from Ang I by NEP. An (increased) endogenous production can also be the result of a gene therapeutic intervention, e.g. by overexpressing ACE2 or a construct that generates directly Ang-(1-7) or one of its precursors. An increased concentration of endogenously produced Ang-(1-7) can also result from a reduced degradation of Ang-(1-7) e.g. by pharmacological inhibition of ACE which degrades Ang-(1-7) to Ang-(1-5).

Recombinant or overexpressed ACE2 will increase the concentration of Ang-(1-7) directly by stimulating its conversion from Ang II. ACE inhibitors will reduce Ang-(1-7) degradation to Ang-(1-5) while AT1a receptor blockers will increase Ang-(1-7) levels by elevation of ACE2 substrate availability.

Further considered are molecules, e.g. peptides or proteins, comprising the Ang-(1-7) peptide sequence or chemical structure.

"Acute lung injury" (ALI) and "acute respiratory distress syndrome" (ARDS) are inflammatory disorders of the lung most commonly caused by sepsis, pneumonia, trauma, and/or aspiration. Inflammation can be locally restricted to the lung, or the pulmonary inflammation can be part of a systemic inflammatory process. ALI and ARDS are characterized by hypoxemia and diffuse infiltrates on chest x-ray in the absence of elevated left atrial pressure. ALI and ARDS differ only in the degree of hypoxemia in that ALI is defined as a ratio of arterial oxygen partial pressure over inspiratory oxygen fraction ($PaO_2/FiO_2$)<300 and ARDS as a $PaO_2/FiO_2$<200 (16). Diagnosis is by clinical presentation, ABGs (arterial blood gas analyses) and imaging studies. Treatment is with lung-protective, low tidal volume mechanical ventilation, supportive therapy, and treatment of underlying causes.

DETAILED DESCRIPTION OF THE INVENTION

Example

Figure 1B:
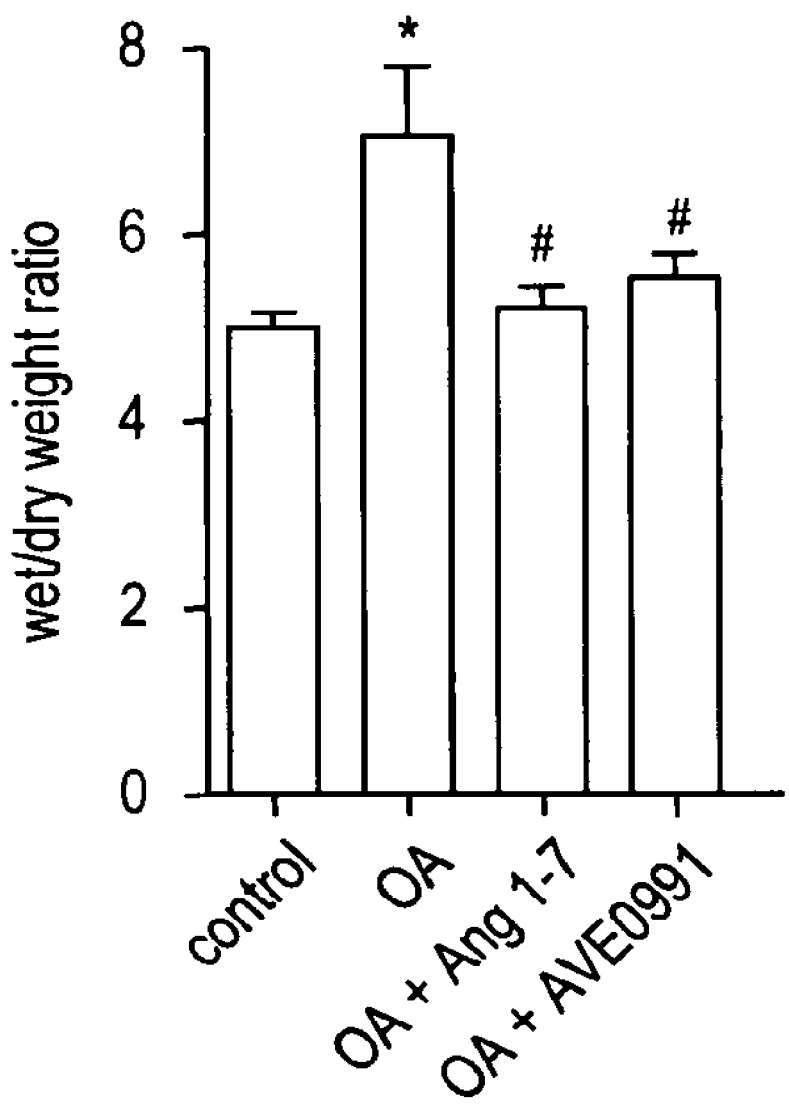
FIG. 1 shows the effects of Ang-(1-7) and the non-peptidic Ang-(1-7) receptor agonist AVE0991 on lung MPO activity (FIG. 1(A)), wet-to-dry weight ratio (FIG. 1(B)), mean arterial pressure (FIG. 1(C)) and pulmonary vascular resistance (FIG. 1(D)) in oleic acid induced acute lung injury. All data are mean±SEM from n=6 animals each; * p<0.05 vs. control; # p<0.05 vs. OA.

Animals. Experiments were performed in male Sprague-Dawley rats (Charles River Wiga GmbH, Sulzfeld, Germany) with a body weight (bw) of 330-360 g. Animals received care in accordance with the Guide for the Care and Use of Laboratory Animals (Institute of Laboratory Animal Resources, 7th edition 1996). The study was approved by the local animal care and use committee.

Surgical Preparation and Hemodynamic Monitoring. Rats were anesthetized by intraperitoneal injection of medetomidine (0.5 mg/kg bw, Domitor®, Dr. E. Graeub AG, Basel, Switzerland), fentanyl (0.05 mg/kg bw, JanssenCilag, Neuss, Germany) and midazolam (5 mg/kg bw, Dormicum®, Roche, Basel, Switzerland) as previously described (17). Following tracheotomy, the trachea was cannulated and ventilation was established (Advanced Animal Respirator, TSE Systems GmbH, Bad Homburg, Germany) with a tidal volume of 6 ml/kg bw at 80 breaths/min. Catheters (internal diameter 0.58 mm; Sims Portex Ltd., Hythe, United Kingdom) were introduced into the left carotid artery and the right internal jugular vein for monitoring of arterial blood pressure (AP), fluid replacement and drug delivery as previously described (18). An ultrasonic flowprobe (Transonic®, Transonic Systems Inc., Ithaca, N.Y.) was placed around the ascending aorta distal to the branching of the coronary arteries for continuous monitoring of cardiac output (CO). After median thoracotomy, a catheter was introduced via the right ventricle into the pulmonary artery for measurement of pulmonary artery pressure (PAP). AP, PAP and CO were continuously recorded by the software package DasyLab 32 (DasyLab, Moenchengladbach, Germany). Pulmonary vascular resistance (PVR) was calculated as arteriovenous pressure differences over flow under the assumption of a constant left atrial pressure of 2 mmHg.

Experimental Groups and Protocol. Rats were randomly assigned to four groups of six animals each: Animals in group 1 (control) did not receive any pharmacological interventions. In group 2 (OA), ALI was induced by intravenous infusion of 0.2 mg/kg oleic acid (Sigma, Munich, Germany) over 30 min in the absence of any treatment. In group 3 (OA+Ang-(1-7)), ALI was induced as in group II, and infusion of Ang-(1-7) at 5 pmol/kg per min was initiated immediately after ALI induction. In group 4 (OA+AVE0991), ALI was induced as in group II, and infusion of AVE0991 at 500 pmol/kg per min was initiated immediately after ALI induction. In two additional groups of n=6 each, in which only myeloperoxidase (MPO) activity was measured, infusion of the Ang-(1-7) receptor blocker A779 (10 pmol/kg per min) was initiated either alone (group 5) or in combination with Ang-(1-7) (5 pmol/kg per min; group 6) immediately after induction of ALI.

After surgical preparation and hemodynamic stabilization over at least 15 min, baseline hemodynamics were recorded and arterial blood gases analyzed (RapidLab 348; Chiron Diagnostics GmbH, Fernwald, Germany). Removed blood volume was replaced by hydroxyethyl starch (6% hydroxyethyl starch 200/0,6; Fresenius, Bad Homburg, Germany). Immediately after baseline recordings, 0.2 mg/kg oleic acid was infused intravenously over 30 min in groups II-VI or an equal volume of 0.9% NaCl in group I. In all groups, measurements were repeated in 60 min intervals up to a total of 4 h at which time animals were sacrificed by exsanguination. After in situ ligation of the right main bronchus, lungs were excised and processed for determination of wet-to-dry weight ratio and myeloperoxidase (MPO) activity as described below.

Assessment of Lung Water and Inflammatory Response. For determination of lung water content, wet-to-dry weight ratio was measured by use of the microwave drying technique (18). Recruitment of inflammatory cells was analyzed by measurements of MPO activity in lung homogenates as previously described (19). In brief, MPO activity was determined by a 3,3'-5,5'-tetramethylbenzidine (TMB)-based photometric assay, compared to appropriate standard curves, and expressed as units per gram lung tissue (U/g).

Statistical Analysis. All data are presented as mean±SEM. Data were tested by Kruskal-Wallis test for differences between groups. Statistical significance was assumed at $P<0.05$.

Figure 1C:
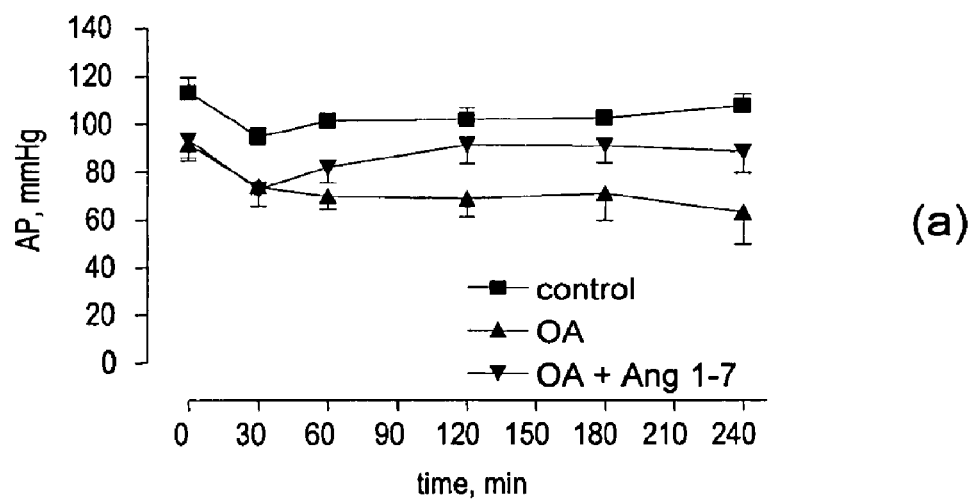
Figure 1C:
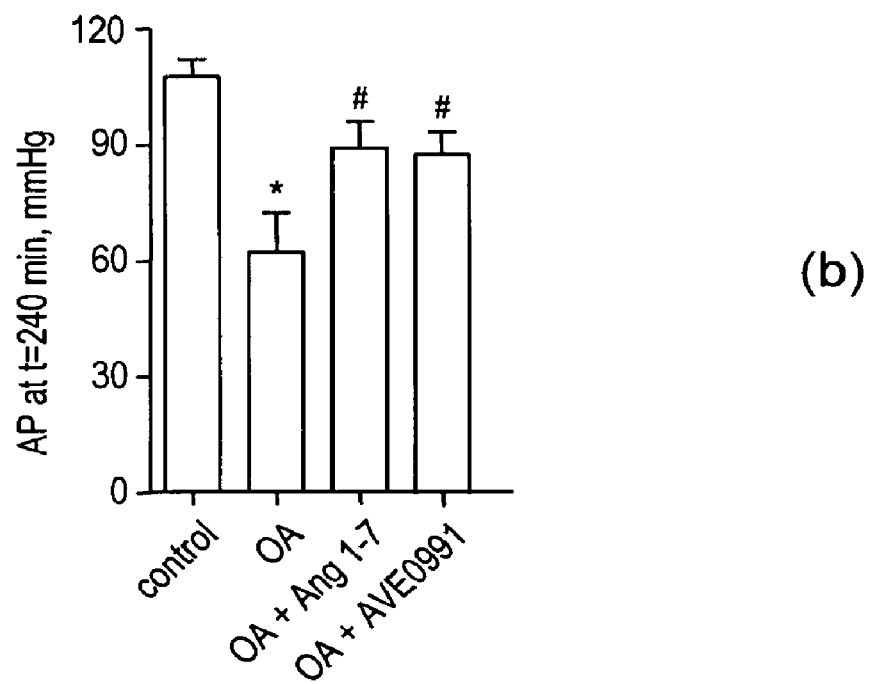
Figure 1D:
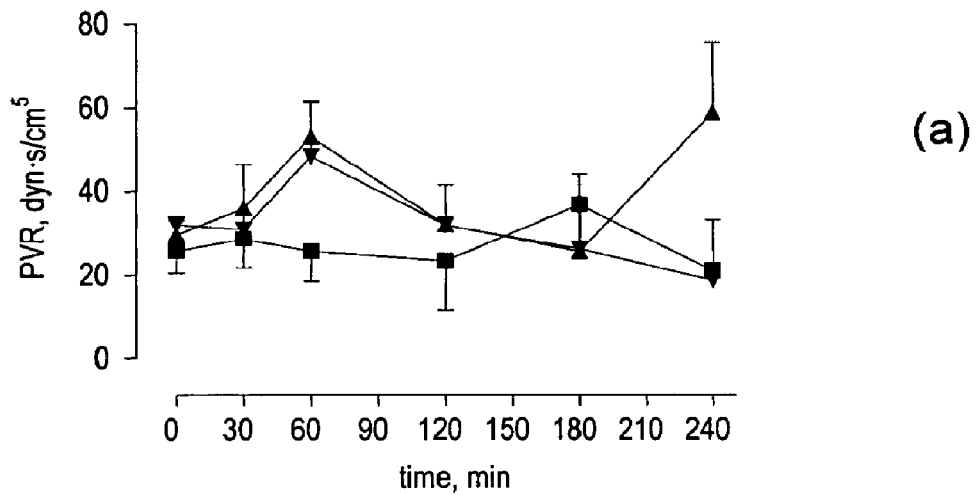
Figure 1D:
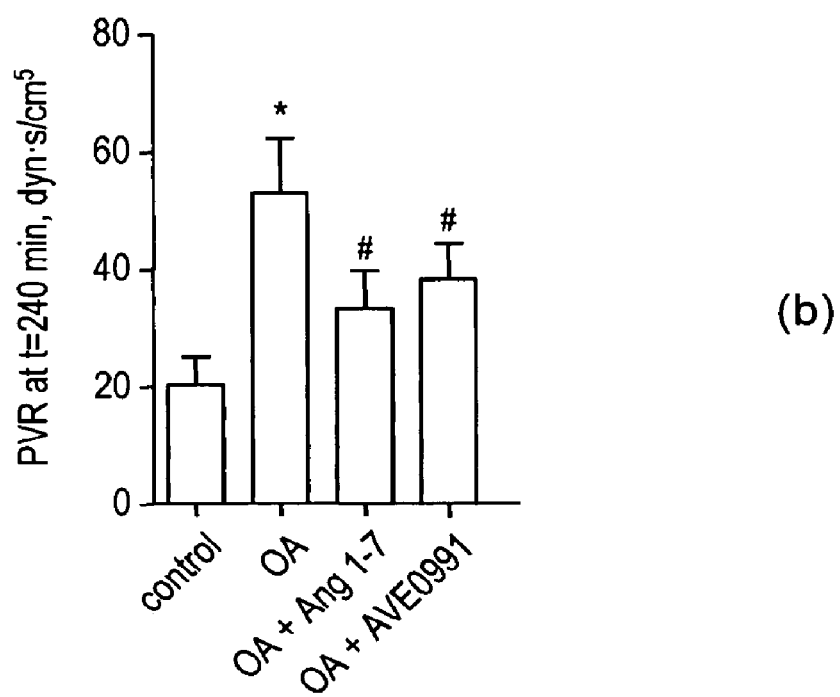

Results. Oleic acid induced ALI as characterized by an increase in MPO activity (FIG. 1(A)), lung wet-to-dry weight ratio (FIG. 1 (B)), and pulmonary vascular resistance (FIG. 1(D)), while systemic arterial pressure was reduced after 4 h as compared to control (FIG. 1(C)). Ang-(1-7) completely prevented the development of OA-induced ALI, as demonstrated by the fact that Ang-(1-7) infusion abrogated OA-induced changes in lung wet-to-dry weight ratio, MPO activity, and pulmonary vascular resistance. The protective effect of Ang-(1-7) was apparently not attributable to its described vasodilatory effect in systemic blood vessels, since Ang-(1-7) infusion attenuated systemic hypotension in OA-infused rats. The non-peptidic Ang-(1-7) receptor agonist AVE0991 similarly attenuated OA-induced ALI. Additional MPO analyses in groups 4 and 5 indicate that blockade of the Mas receptor by A779 aggravates OA-induced ALI, and blocks the rescue effect of Ang-(1-7) infusion.

Conclusions. The present findings show that infusion of Ang-(1-7) or a non-peptidic Ang-(1-7) receptor agonist completely prevents lung oedema and inflammation in an experimental model of oleic-acid induced ALI. This protective effect is mediated via the G-protein coupled receptor Mas, since it is lost after Mas blockade by A779. Endogenously formed Ang-(1-7) serves as an intrinsic protection mechanism against ALI, which is aggravated after Mas blockade by A779.

The invention claimed is:

1. A peptide comprising the amino acid sequence of $Asp^1$-$Arg^2$-$Val^3$-$Ser^4$-$Ile^5$-$His^6$-$Cys^7$ (SEQ ID NO: 4).

2. A pharmaceutical composition comprising a peptide according to claim 1 and a pharmaceutically acceptable carrier.

3. The pharmaceutical composition of claim 2, wherein the pharmaceutical composition is formulated for oral, intramuscular, intravenous, subcutaneous, topical, transdermal, rectal, vaginal, pulmonary, intranasal, intrabuccal, or sublingual administration.

4. The pharmaceutical composition of claim 2, wherein the pharmaceutical composition is formulated for oral administration.

5. The pharmaceutical composition of claim 2, wherein the pharmaceutical composition is formulated for intravenous administration.

6. The pharmaceutical composition of claim 2, wherein the pharmaceutical composition is formulated as a tablet, pill, capsule, granules, a syrup, a spray, an aerosol, a liposomal composition, an ointment, a suppository, an implant, a plaster, or a slow release formulation.

7. The pharmaceutical composition of claim 2, wherein the pharmaceutical composition further comprises one or more pharmacologically inert and pharmacologically acceptable excipients selected from a polymer carrier, a disintegration agent, a lubricant, a solvent, or a swelling agent.

* * * * *